United States Patent [19]

Decor et al.

[11] Patent Number: 5,147,444
[45] Date of Patent: Sep. 15, 1992

[54] HERBICIDAL COMPOSITIONS BASED ON A GLYPHOSATE HERBICIDE AND ACIFLUORFEN

[75] Inventors: Jean-Pierre Decor, Thurins; Guy Borrod, Lyons, both of France

[73] Assignee: Rhone Poulenc Agrochimie, Lyons, France

[21] Appl. No.: 701,630

[22] Filed: May 14, 1991

Related U.S. Application Data

[63] Continuation of Ser. No. 326,909, Mar. 22, 1989, abandoned, which is a continuation-in-part of Ser. No. 927,070, Nov. 4, 1986, abandoned, which is a continuation-in-part of Ser. No. 879,685, Jun. 27, 1986, abandoned.

[51] Int. Cl.$^5$ .................... A01N 57/12; A01N 37/10
[52] U.S. Cl. .......................... 71/86; 71/115
[58] Field of Search ................ 71/86, 115, 116

[56] References Cited

U.S. PATENT DOCUMENTS

| 4,063,929 | 12/1977 | Bayer et al. | 71/115 |
| 4,233,054 | 11/1980 | Szczepanski et al. | 71/98 |
| 4,350,522 | 9/1982 | Bayer et al. | 71/116 |

FOREIGN PATENT DOCUMENTS

| 143547 | 6/1985 | European Pat. Off. | |
| 192583 | 8/1986 | European Pat. Off. | |
| 8403607 | 9/1984 | PCT Int'l Appl. | 71/86 |
| 2169806 | 8/1987 | United Kingdom | |

OTHER PUBLICATIONS

Sandberg, et al., "Glyphosate and Other Herbicides for Reduced Tillage", (1985), pp. 86–89.

*Primary Examiner*—Richard L. Raymond
*Assistant Examiner*—S. Mark Clardy
*Attorney, Agent, or Firm*—Morgan & Finnegan

[57] ABSTRACT

The invention relates to herbicidal compositions containing a glyphosate type herbicide and a phenoxybenzoic type herbicide, preferably acifluorfen-sodium, the ratio by weight of phenoxybenzoic type herbicide:glyphosate type herbicide ranging between about 1:12 and about 1:80. The compositions are relatively fast-acting and resistant to being washed out during rainfall occurring shortly after application. The invention also relates to a method of weed control employing the compositions.

21 Claims, No Drawings

HERBICIDAL COMPOSITIONS BASED ON A GLYPHOSATE HERBICIDE AND ACIFLUORFEN

CROSS REFERENCE TO RELATED APPLICATIONS

This is a continuation of co-pending application Ser. No. 326,909, filed on Mar. 22, 1989 which is a continuation-in-part of co-pending application Ser. No. 927,070, filed Nov. 4, 1986, which is a continuation-in-part of abandoned application Ser. No. 879,685, filed Jun. 27, 1986, which are incorporated herein by reference.

BACKGROUND OF THE INVENTION

The present invention relates to new herbicidal compositions comprising a glyphosate type herbicide and a phenoxybenzoic type herbicide. It also relates to methods for the treatment of undesirable plants using these compositions.

Glyphosate (i.e. N-phosphonomethylglycine) and its salts are well known wide spectrum herbicides which are active against annual and perennial weeds. This class of herbicides is well known for its post-emergence efficacy and is used for agricultural and garden applications. Nevertheless, it is still desirable to improve the herbicidal activity of these compounds.

It is known that glyphosate type herbicides act relatively slowly. In fact, a period of approximately three weeks is generally required before the effects are observed.

In order to overcome this disadvantage, PCT Patent Application WO 84/03,607 indicates that in the specific case of application to amateur gardens, the addition of a certain quantity of acifluorfen or one of its salts to glyphosate type herbicides increases the speed of action of such herbicides. In this context, an herbicidally effective quantity of glyphosate type herbicide is employed and acifluorfen is added so that the ratio by weight of glyphosate to acifluorfen is in practice between 1:8.33 and 4.2. However, it is observed that the compositions described reveal a marked antagonism in many cases, which results in the efficacy of the glyphosate type herbicide being adversely affected. The use of extemporaneous mixtures of glyphosate and acifluorfen against weeds of field crops such as soybeans, and not of garden weeds, has also been proposed. Thus, the publication: Proceedings, Southern Weed Science Society, 38th annual meeting, Sandberg et al., 1985, pages 86–89, indicates that 430 g/ha of glyphosate combined with 70 g/ha of acifluorfen shows a marked antagonism against the weeds tested. This antagonism decreases, however, when the glyphosate:acifluorfen ratio decreases, i.e. when the quantity of acifluorfen is increased.

A second publication, Ibid, pages 64–67, Frost, also confirms the fact that it is necessary to increase the dose of acifluorfen.

It is also seen from the latter publication that the spectrum of activity of glyphosate is reduced, especially against graminaceous plants.

Another disadvantage related to the mode of action of glyphosate or its derivatives lies in the fact that it can very easily be washed out, i.e. if there is heavy rainfall within a few hours of its application, a large part of it is removed. It is also desirable to improve the action of glyphosate type herbicides on plants whose growth is slowed down by low temperatures and/or low humidity, or on plants which are at the end of their growth cycle.

In an unexpected way, the present invention enables these disadvantages to be overcome and more particularly, enables one or more of the following advantages to be achieved:

1. increase in the speed of action of glyphosate type herbicides;
2. improvement in the activity spectrum of glyphosate type herbicides;
3. improvement in the herbicidal properties of glyphosate type herbicides;
4. prevention of glyphosate type herbicides from being washed out; and
5. improvement in the activity of glyphosate type herbicides on plants whose growth is slowed down by low temperatures and/or low humidity or on plants which are at the end of their growth cycle.

SUMMARY OF THE INVENTION

The present invention accordingly provides a herbicidal composition which comprises a glyphosate type herbicide (A) and a phenoxybenzoic type herbicide (B), wherein the ratio by weight of phenoxybenzoic type herbicide to glyphosate type herbicide is from about 1:12 to about 1:80 and preferably from about 1:15 to about 1:50.

This is equivalent to a molar ratio (B):(A), taking into account the molar equivalence calculated on the basis of the acids for (A) as well as for (B) of from about 1.2:12 to about 1.2:80 and preferably from about 1.2:15 to about 1.2:50.

DETAILED DESCRIPTION OF THE INVENTION

The glyphosate type herbicides which may be employed in the present invention are generally compounds of formulae I and Ia below, as well as their metabolites and derivatives:

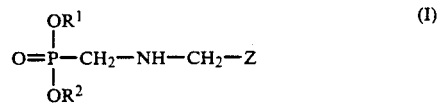

wherein

Z is cyano or COOR;

R is a hydrogen atom; lower alkyl; lower alkenyl; lower alkoxyalkyl; aryl (e.g. phenyl) having 6 to 10 carbon atoms and being unsubstituted or substituted by 1 to 3 substituents chosen independently from lower alkyl, lower alkoxy, halo, trifluoromethyl, nitro and cyano; or a salt-forming cation; and $R^1$ and $R^2$, which are identical or different, are a hydrogen atom; lower alkyl; aryl having 6 to 10 carbon atoms and being unsubstituted or substituted by 1 to 3 substituents chosen independently from lower alkyl, lower alkoxy, halogen, trifluoromethyl, nitro and cyano; biphenyl; or an herbicidally-acceptable salt-forming cation; or

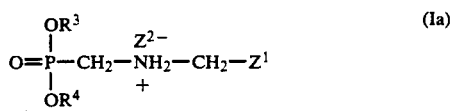

wherein $Z^2$ is an herbicidally acceptable salt-forming anion;

$R^3$ and $R^4$, which are identical or different, are a hydrogen atom; lower alkyl; aryl having 6 to 10 carbon atoms and being unsubstituted or substituted by 1 to 3 substituents chosen independently from lower alkyl, lower alkoxy, halogen, trifluoromethyl, nitro and cyano; or biphenyl; and $Z^1$ is cyano or $COOR^5$, wherein $R^5$ is as hereinbefore defined for R, except that $R^5$ is not a cation.

The preferred compounds of formula I and Ia are those in which Z and $Z^1$ are COOR and $COOR^5$ respectively. With regard to formula I, the preferred compounds are those in which R, $R^1$ and $R^2$, which may be identical or different, are a hydrogen atom or an herbicidally acceptable cation. Organic ammonium salts of formula I, especially those in which R is a cation derived from isopropylamine, give good results and are available on the market. Organic sulphonium or sulphoxide salts (e.g. those in which $R^1$ and/or $R^2$ are the trimethylsulphonium cation or trimethylsulphoxide cation) are also suitable. An example of a compound of formula I or Ia is the isopropylamine salt of N-(phosphonomethyl)glycine which is the active ingredient in the herbicide marketed by Monsanto under the trade name Roundup.

With regard to formula Ia, the preferred compounds are those in which $R^3$ and $R^4$, which may be identical or different, are lower alkyl or aryl (e.g. phenyl), and in which $Z^1$ is $COOR^5$, wherein $R^5$ is lower alkyl or aryl.

Suitable salt-forming cations and anions within the definitions of R, $R^1$, $R^2$ and $Z^2$ are compatible from a herbicidal point of view and do not vitiate the herbicidal properties of the compounds. The salified form is generally more soluble in water and more advantageous than the free acid or the corresponding free base.

Examples of suitable cations include alkali metal cations such as sodium or potassium; alkaline earth metal cations such as calcium or magnesium; and cations of copper, zinc, iron, nickel, manganese, ammonium or organic ammonium, phosphonium, sulphonium or sulphoxide, these cations preferably having a molecular weight less than 300. Suitable organic cations of ammonium include amine derivatives, especially aliphatic, cyclic or heterocyclic amines containing 1 or 2 amine groups, such as alkylamines, alkyleneamines, alkenylamines and alkanolamines. Examples of amine derivatives include methylamine, ethylamine, n-propylamine, iso-propylamine, n-butylamine, iso-butylamine, sec-butylamine, n-amylamine, iso-amylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diiso-propylamine, di-n-amylamine, diiso-amylamine, dihexylamine, diheptylamine, dioctylamine, trimethylamine, triethylamine, tri-n-propylamine, triisopropylamine, tri-n-butylamine, triiso-butylamine, tri-sec-butylamine, tri-n-amylamine, n-propanolamine, isopropanolamine, diethanolamine, N,N'-diethylethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine and propylenediamine, primary aromatic amines such as aniline, methoxyaniline, ethoxyaniline, ortho-, meta- and para-toluidine, phenylenediamine, 2,4,6-tribromoaniline, benzidine, naphthylamine, and ortho-, meta- and para-chloroaniline, and heterocyclic amines such as pyridine, morpholine, piperidine, pyrrolidine, indoline and azepine.

Among suitable organic cations of sulphonium and sulphoxide are $C_1$ to $C_{10}$ alkyl (preferably $C_1$ to $C_5$ alkyl) sulphonium cations and $C_1$ to $C_{10}$ alkyl (preferably lower alkyl) sulphoxide cations, such as trimethylsulphonium, ethyldimethylsulphonium, tripropylsulphonium, trimethyl sulphoxide and triethyl sulphoxide. These salts are described in particular in U.S. Pat. No. 4,315,765. Suitable phosphonium cations include those represented by the formula:

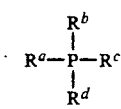

wherein $R^a$, $R^b$, $R^c$ and $R^d$, which may be identical or different, are phenyl or $C_1$ to $C_{10}$ alkyl radicals, preferably lower alkyl. These salts are described in U.S. Pat. No. 4,341,549. Other examples of suitable cations are described in U.S. Pat. No. 3,799,758. Compatible anions which are suitable include chloride, bromide, fluoride, sulphate, sulphite, bisulphite, phosphate, orthophosphate, carbonate, bicarbonate, acetate, butyrate, benzoate and maleate anions.

Examples of compounds of formulae I and Ia are described in U.S. Pat. Nos. 3,799,758, 3,835,000, 3,950,402, 4,067,719, 4,008,296, 4,147,719 and 4,369,142.

A large number of compounds which are metabolized by green plants or which function in a manner equivalent to that of the active part (from a phytotoxic point of view) of glyphosate may also be employed. These compounds include, for example, compounds represented by formulae I and Ia and the following formulae:

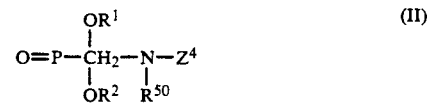 (II)

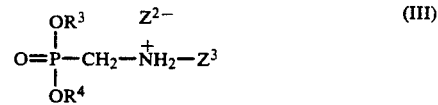 (III)

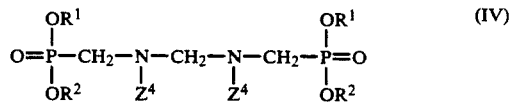 (IV)

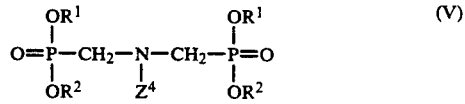 (V)

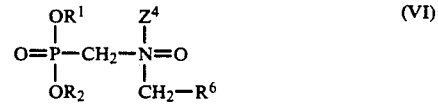 (VI)

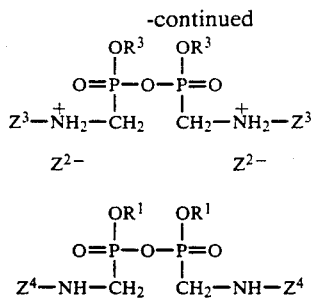

wherein:

$Z^2$, $R^1$, $R^2$, $R^3$ and $R^4$ are as hereinbefore defined;

$Z^4$ is $CH_2CN$; CONHOH (or its tautomeric form $-C(OH)=NOH$); $CH_2COOR$, wherein R is as hereinbefore defined; or $CONR^7R^8$, wherein $R^7$ and $R^8$, which may be identical or different, are as hereinbefore defined for R;

$Z^3$ is $-CH_2-CN$; $-CO-NHOH$ (or its tautomeric form $-C(OH)=NOH$); $-CH_2-COOR^5$; or $-CONR^5R^5$ wherein the groups $R^5$, which may be identical or different, are as hereinbefore defined; and $R^{50}$ is lower alkyl, lower alkoxy, hydroxy, lower alkanoyl, substituted or unsubstituted arylcarbonyl, trifluoroacetyl, lower alkylthioalkanoyl, amino, alkylamino, nitro, nitroso, or radical $-COOR^9$, $-OCH_2-COOR^{10}$, $-CH_2P(O)OR^{15}(OR^{25})$, $-S(O)_m-R^{11}$, $-SO-X-R^{11}$ or $-CO-S(O)_m-R^{12}$, wherein $R^9$ is lower alkyl, lower alkenyl or unsubstituted or substituted aryl group; and $R^{11}$ is lower alkyl or unsubstituted or substituted aryl group; X is $-O-$ or $-S-$; and $R^{12}$ is lower alkyl, lower alkenyl, lower alkynyl, unsubstituted or substituted aryl or unsubstituted or substituted (lower) arylalkyl; m is 0, 1 or 2; $R^{15}$, $R^{25}$ and $R^{10}$ are as hereinbefore defined for $R^1$; $R^6$ is a hydrogen atom, lower alkyl, unsubstituted or substituted aryl, unsubstituted or substituted lower arylalkyl, $COOR^5$ or $-P(O)(OR^3)(OR^4)$, wherein $R^3$, $R^4$ and $R^5$ are as hereinbefore defined.

Compounds of formulae II to VIIa are generally known and may be prepared by known methods or similar methods. These products and methods are described in U.S. Pat. Nos. 4,035,177, 4,062,669, 4,175,946, 4,251,258, 4,231,782, 4,322,238, 4,322,239, 4,323,387, 4,300,942, 4,300,943 and 4,414,158; Research Disclosure No. 220,001 (Derwent No. 73,821 E/35); United Kingdom Patent Nos. 2,090,596 and 2,072,179; and Japanese Patent Nos. 56,139,408, 57,120,595 and 57,099,597 (Derwent Nos. 8191755D, 8273692E and 8262700E).

The (phenoxy-substituted) benzoic derivatives which may be employed in the present invention include 2-nitro-5-phenoxy substituted benzoic acids and their derivatives, of formula VIII below.

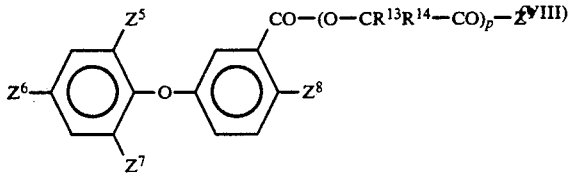

wherein:
$Z^5$ is chlorine or fluorine;
$Z^6$ is chlorine or $CF_3$;
$Z^7$ is hydrogen, chlorine or fluorine;
$Z^8$ is chlorine or nitro;
p is 0 or 1;
$R^{13}$ and $R^{14}$, which may be identical or different, are hydrogen or methyl; and
$Z^9$ is hydroxy, alkoxy (especially lower alkoxy), (lower) alkanesulphonamido or OM (M being an atom of an alkali metal or alkaline earth metal, more particularly Na or K).

Among these compounds, compounds of formula VIII wherein $Z^6$ is $CF^3$, $Z^8$ is nitro, $Z^5$ is chlorine and $Z^7$ is hydrogen are preferred, because these more particularly meet the objectives of the present invention listed in the preamble.

Among these, the following are preferred: acifluorfen, wherein p is O, $R^{13}$ and $R^{14}$ are hydrogen and $Z^9$ is hydroxy; or the potassium or sodium salts of acifluorfen, wherein $Z^9$ is OM and M is Na or K; fomesfen, wherein p is 0 and $Z^9$ is methanesulphonamido ($-NH-SO_2CH_3$); lactofen and benzofluorfen, wherein p is 1, $R^{13}$ and $R^{14}$ are hydrogen and $Z^9$ is OEt. Among the latter, acifluorfen-sodium is preferred.

The herbicidal compositions of the present invention which comprise a glyphosate type herbicide and a phenoxybenzoic type herbicide may contain mixtures of the active substances and known ingredients such as surfactants, carriers and diluents. The compositions generally comprise the active ingredients in association with a herbicidally acceptable diluent or carrier. If the composition contains two active ingredients, the systemic glyphosate herbicide and the phenoxybenzoic derivative, or more than two active ingredients, it is desirable that the compositions are suitably mixed to achieve homogeneity. The compositions of the invention may be in the form of a mixture comprising both the glyphosate and phenoxybenzoic compound. Alternatively, the glyphosate and phenoxybenzoic compounds may be provided separately, for example in the form of a pack or kit containing each of the compounds for tank-mixing prior to application or for separate or sequential application.

The present invention also relates to a weed control method which comprises applying an effective quantity of a herbicidal composition to the weeds to be destroyed. The method is applied with the object of destroying the weeds and enables, in particular, weed growth to be controlled and where appropriate, the weeds to be totally or partially destroyed.

The herbicidal compositions or mixtures of active substances, as described above and which can be used according to the present invention, are applied in a suitable manner to plant leaves and in particular to the weeds to be destroyed, for example when the latter carry green foliage.

The herbicidal compositions may also be applied shortly before harvest in order to kill weeds having roots which persist in the soil after harvest. Thus, the invention makes it possible to plant shortly after harvest without having to carry out mechanical weeding operations (manual or otherwise). However, this method is reserved for cases in which the applied herbicides do not leave residues and/or are not selective against the crops to be planted after the harvest.

In general, the systemic glyphosate type compound is applied to plants at rates from about 0.1, preferably about 0.3, to about 0.9 kg/ha, more preferably from approximately 0.4 to approximately 0.8 kg/ha and especially from approximately 0.5 to approximately 0.7 kg/ha.

Compounds of formula VIII are used as chemical substances which modify membranes, and are applied in doses from approximately 0.004 to approximately 0.08 kg/ha and preferably from approximately 0.01 to approximately 0.05 kg/ha.

The ratio by weight of phenoxybenzoic type herbicide to glyphosate type herbicide is from about 1:12 to about 1:80 and preferably from about 1:15 to about 1:50.

The invention provides compositions which have a good resistance to being washed out by rain after application; and compositions which have a high activity on plants at the end of their growth cycle and/or plants having a slow growth rate.

Using the compositions of the present invention, an effective control of the following weeds is observed: Dicotyledonous plants: Xanthium, Ipomoea, Sesbania, Abutilon, Polygonum, Amaranthus, Chenopodium, Sinapis, Datura, Solanum, Euphorbia, Bidens and Galinsoga; and Monocotyledonous plants: (graminaceous plants) Setaria and Echinochloa.

The present invention provides a method for the control of the growth of weeds at a locus which comprises applying thereto, post-emergence of the weeds, about 0.1, preferably about 0.3, to about 0.9 kg/ha of a glyphosate type herbicide and about 0.004 to about 0.08 kg/ha of a phenoxybenzoic type herbicide, the ratio of phenoxybenzoic herbicide to glyphosate type herbicide being from about 1:12 to about 1:80 by weight.

The invention also provides a method for the control of the growth of weeds at a locus, the weeds being at the end of their growth cycle and/or having their growth slowed down by low temperatures and/or low humidity. The method comprises applying thereto about 0.1, preferably about 0.3, to about 0.9 kg/ha of a glyphosate type herbicide and about 0.004 to about 0.08 kg/ha of phenoxybenzoic herbicide, the ratio of phenoxybenzoic type herbicide to glyphosate type herbicide being from about 1:12 to about 1:80 by weight.

Another feature which the invention provides is a method for reducing wash out by rainfall of a glyphosate type herbicide after post-emergence application to control the growth of weeds at a locus which comprises applying thereto about 0.1, preferably about 0.3, to about 0.9 kg/ha of a glyphosate type herbicide and about 0.004 to about 0.08 kg/ha of a phenoxybenzoic type herbicide, the ratio of phenoxybenzoic type herbicide to glyphosate type herbicide being from about 1:12 to about 1:80 by weight.

The methods according to the present invention make it possible to control a wide spectrum of monocotyledonous or dicotyledonous annual and perennial weeds. The weeds may be destroyed by the methods and the compositions of the present invention, enabling the field to be left in good condition for the subsequent growth of crops such as cereals, wheat, rice, cotton, soybeans, beets (especially sugarbeets), sunflowers, rapeseeds, sugarcane and vegetable crops, and for achieving an effective weed control in perennial crops (grape vines and orchards).

Because the herbicidal effect appears and becomes effective shortly after treatment (much earlier than with glyphosate type herbicide alone, even when it is employed in higher doses), the method and the composition according to the present invention also make it possible to control plants, especially weeds, quickly.

The method according to the present invention also makes it possible to prevent glyphosate or its derivatives from being washed out. The invention provides a method which makes it possible to prevent glyphosate or one of its derivatives, for example compounds of formula I or Ia, from being washed out, comprising applying glyphosate or one of its derivatives, and a phenoxybenzoic type compound, for example compounds of formula VIII, using the doses and ratios by weight defined above.

When the method of the present invention is put into practice, the herbicidal compositions generally contain one or more ingredients other than the glyphosate type and phenoxybenzoic type compounds and their derivatives (hereinafter referred to as active ingredients). These compositions, which may be employed as herbicidal agents, generally contain the active ingredients in association with solid or liquid carriers which are acceptable in agriculture and surface-active agents which are acceptable in agriculture. The usual inert carriers and surface-active agents may be employed. These compositions form part of the present invention.

The composition may also contain other ingredients such as protective colloids, adhesives, thickeners, thixotropic agents, agents which facilitate penetration, activators, stabilizers, and sequestering agents as well as other known active ingredients having pesticidal properties (especially insecticides, fungicides or herbicides) or plant growth regulating properties. More generally, the compositions employed in the present invention may contain all the solid or liquid additives corresponding to conventional methods of formulation.

In the following description of the present invention, unless otherwise stated, the percentages are expressed on a weight basis.

The compositions of the invention may also contain activators. The activators are compounds which do not have herbicidal properties at normal doses (approximately 0.5 kg/ha to approximately 5 kg/ha), but which have a capacity to increase significantly the herbicidal activity of glyphosate type compounds. Most of these activators are well known. As described below, some activators are surfactants, especially ethylene oxide polycondensate derivatives of phenols, alcohols or amines. Some activators are ammonium salts, especially chlorides, sulphates and inorganic or organic phosphates of ammonium. Other activators may be employed. The activators which normally increase the herbicidal activity of glyphosate type compounds are also useful in the present invention when phenoxynitrobenzoic acid derivatives are employed. The quantity of activators employed in the compositions of the present invention is generally from approximately 0.1% to approximately 500% of the quantity of the glyphosate type compound and preferably from approximately 50% to approximately 350%. This percentage depends on the specific nature of the activators employed.

In general, the compositions according to the present invention usually contain approximately 0.05% to approximately 95% of one or more active ingredients according to the present invention, approximately 1% to approximately 95% of one or more solid or liquid carriers and optionally, approximately 0.1% to approximately 50% of one or more surface-active agents.

The compositions preferably contain about 10% to about 50% by weight of the combination of the glyphosate type and phenoxybenzoic type herbicides, preferably compounds of formulae I and VIII, and more preferably about 15% to about 30%.

As mentioned above, the active ingredients employed in the present invention are generally combined with carriers and optionally with surface-active agents.

In the description of the invention, the term "carrier" denotes a natural or synthetic organic or inorganic ingredient with which the active ingredients are combined in order to facilitate application to the plant or the soil. This carrier is generally inert and must be acceptable in agriculture, especially with respect to the plant treated. The carrier may be solid (e.g. clays, natural or synthetic silicates, silica, resins, waxes, and solid fertilizers) or liquid (e.g. water and alcohols, especially butanol); esters, especially methylglycol acetate; ketones, especially cyclohexanone and isophorone; petroleum fractions; aromatic or paraffinic hydrocarbons, especially xylenes; chlorinated aliphatic hydrocarbons, especially tricholoroethane, or chlorinated aromatic hydrocarbons, especially chlorobenzenes; water-soluble solvents such as dimethylformamide, dimethyl sulphoxide or N-methylpyrrolidone; and liquefied gases.

The surface-active agent may be an emulsifier, dispersant or wetting agent of ionic or nonionic type, or alternatively, a mixture of these surface-active agents. Examples include polyacrylic acid salts, lignosulphonic acid salts, phenolsulphonic or naphthalenesulphonic acids, products of polycondensation of ethylene oxide with fatty alcohols, fatty acids or fatty amines, substituted phenols (especially alkylphenols or arylphenols), sulphonosuccinic acid ester salts, taurine derivatives (especially aklyl taurates), phosphoric esters of alcohols or products of polycondensation of ethylene oxide with phenols, esters of fatty acids with polyhydric alcohols, and derivatives having sulphate, sulphonate and phosphate groups, of the compounds above. The presence of at least one surface-active agent is generally preferred.

The active ingredients of the present invention are generally applied in the form of compositions. These compositions are themselves in different solid or liquid forms. Forms of the compositions include water-soluble powders (having an active ingredient content which may reach 80%) and water-soluble granules especially those obtained by extrusion, compacting, impregnation of a granular carrier, or by granulation starting with a powder (the active ingredient content in these granules being from approximately 0.5% to approximately 80%) and aqueous solutions.

The water-soluble concentrates or solutions (especially powders or granules) also generally contain approximately 5% to approximately 80% of active ingredients, whereas the emulsions or solutions which are ready for application generally contain approximately 0.01% to approximately 20% of active ingredients. In addition to the solvent, the solutions or concentrates may contain approximately 2% to approximately 50% of suitable additives such as stabilizers, surface-active agents, agents facilitating penetration, corrosion inhibitors, colouring agents or adhesives.

Irrespective of the concentration required, emulsions which are particularly suitable for application to plants may be prepared from these concentrates by diluting with water.

The aqueous dispersions, solutions or mixtures may be applied to crop plants to be weeded, by any suitable means, for example by spraying, at rates which are generally of the order of approximately 100 l/ha to approximately 1,200 l/ha of spraying mixtures.

The compositions according to the present invention are suitably applied to the vegetation and especially to the weeds to be destroyed, when the latter carry green foliage.

The following examples illustrate the invention.

EXAMPLE 1:

Application of the Herbicidal Composition After the Germination of Different Species of Plants (in a Glasshouse)

$7 \times 7 \times 8$ cm pots were filled with light sand for cropping, and a certain number of seeds, depending on the plant species and the seed thickness, were planted.

The seeds were then covered with an approximately 3 mm thick layer of soil, and the seeds were allowed to germinate until they reach a convenient stage of growth. The treatment stage for graminaceous plants is the "second-leaf formation" stage. The treatment stage for dicotyledonous plants is the "cotyledon opening and first true leaf development" stage.

The pots were then treated by spraying a quantity corresponding to an application rate of 500 l/ha by volume, containing the active substances at their desired concentrations. The spraying mixture contained a tank-mix, prepared by mixing:

water, an aqueous solution containing 240 g/l of acifluorfen-sodium (the concentration in g/l as well as the doses in g/ha refer to the acid form of acifluorfen), and an aqueous solution containing 360 g/l of the isopropylammonium salt of N-phosphonomethylglycine (which is the acid form of glyphosate; the concentration in g/l as well as the doses in g/ha refer to the acid form), and 15% of a surfactant of the ethylene oxide polycondensate derivative type.

Different active substance concentrations of the spraying liquid were employed, corresponding to the different doses of active substances applied.

The treated pots were then placed in tanks designed to receive irrigation water by sub-irrigation and they were maintained at ambient temperature for 29 days at a relative humidity of 70%.

At 13 days after treatment (T+13) and 29 days after treatment (T+29), the number of live plants in the pots treated with the spraying liquid containing the active substances to be tested were counted and the number of live plants in a control pot treated under the same conditions, but with a spraying liquid which did not contain the active substances were also counted. A percentage equal to 100% indicates that there was total destruction of the plant species under consideration, and a percentage equal to 0% indicates that the number of live plants in the treated pot was identical to that in the control pot.

The plant species used in Example 1 were Morning Glory (Ipomoea purpurea) and Potherb Purslane (Portulaca oleracea).

The tests carried out demonstrate the remarkably early herbicidal effect of the compositions according to the present invention in post-emergence treatments. The following results were obtained.

TABLE 1

| Weed and dates of treatment | glypho-sate doses g/ha | no acifluor-fen | acifluorfen: 10 g/ha | | | |
|---|---|---|---|---|---|---|
| | | | Ipomoea | | Portulaca | |
| | | | T + 13 | T + 29 | T + 13 | T + 29 |
| | | | 0 | 0 | 10 | 10 |
| Ipomoea | 125 | | | | | |

TABLE 1-continued

| Weed and dates of treatment | glyphosate doses g/ha | no acifluorfen | acifluorfen: 10 g/ha | | | |
|---|---|---|---|---|---|---|
| | | | Ipomoea | | Portulaca | |
| | | | T + 13 0 | T + 29 0 | T + 13 10 | T + 29 10 |
| T + 13 | | 0 | 0 | — | — | — |
| T + 29 | | 0 | — | 0 | 0 | — |
| Portulaca | 125 | | | | | |
| T + 13 | | 0 | — | — | 80 | — |
| T + 29 | | 10 | — | — | — | 80 |
| Ipomoea | 250 | | | | | |
| T + 13 | | 0 | 20 | — | — | — |
| T + 29 | | 0 | — | 20 | — | — |
| Portulaca | 250 | | | | | |
| T + 13 | | 0 | — | — | 98 | — |
| T + 29 | | 20 | — | — | — | 95 |

TABLE II

| Weed and dates of treatment | glyphosate doses g/ha | no acifluorfen | acifluorfen: 20 g/ha | | | |
|---|---|---|---|---|---|---|
| | | | Ipomoea | | Portulaca | |
| | | | T + 13 0 | T + 29 0 | T + 13 20 | T + 29 10 |
| Ipomoea | 125 | | | | | |
| T + 13 | | 0 | 0 | — | — | — |
| T + 29 | | 0 | — | 80 | — | — |
| Portulaca | 125 | | | | | |
| T + 13 | | 0 | — | — | 90 | — |
| T + 29 | | 10 | — | — | — | 90 |
| Ipomoea | 250 | | | | | |
| T + 13 | | 0 | 98 | — | — | — |
| T + 29 | | 0 | — | 80 | — | — |
| Portulaca | 250 | | | | | |
| T + 13 | | 0 | — | — | 100 | — |
| T + 29 | | 20 | — | — | — | 100 |

EXAMPLE 2:

Field Experiments

The field was divided into 5 meter squared plots. Several species were sown in each plot, in rows 15 cm apart. The species included the following monocotyledonous weeds:

| Wild oat: *Avena fatua* | (AVEFA) |
|---|---|
| Cockspur grass: *Echinochloa crus-galli* | (ECHCG) |
| Ryegrass: *Lolium multiflorum* | (LOLMU) |
| Panic grass: *Panicum miliaceum* | (PANMI) | and the following dicotyledonus weeds:

| Pigweed: *Amaranthus retroflexus* | (AMARE) |
|---|---|
| Wild mustard: *Sinapis arvensis* | (SINAR) |

When all the plants reached the 2-3 leaf stage, i.e. approximately 3 weeks after sowing, treatments were applied by preparing tank mixes of active ingredients at suitable concentrations and spraying them on the rows of plants at a volume of 500 l/ha in order to obtain adequate rates. An untreated plot was placed in contiguity with each treated plot for comparison and rating. The ratings were carried out at different times after the treatment and are expressed as percentages of destruction for each species, in comparison with the same species in the untreated plot.

In this specific example, rain (20 mm water) washed the plants 15 hours after treatment. The herbicidal effect was observed 5 days after treatment. The same active ingredients were used as in the previous example. The following results were obtained:

TABLE III

| Active Ingredients | Doses g/ha | AVEFA | ECHCG | LOLMU | PANMI | AMARE | SINAR |
|---|---|---|---|---|---|---|---|
| acifluorfen sodium | 50 | 9 | 7.5 | 6.5 | 7.5 | 25 | 22.5 |
| mixture of both active glyphosate salt formulation and acifluorfen sodium solution | 200 + 5 | 27.5 | 35 | 37.5 | 37.5 | 60 | 40 |
| | 400 + 5 | 70 | 67.5 | 62.5 | 67.5 | 70 | 65 |
| | 400 + 20 | 70 | 70 | 62.5 | 72.5 | 85 | 72.5 |

What is claimed is:

1. A herbicidal composition, comprising
(a) a glyphosate herbicide of formula I or Ia:

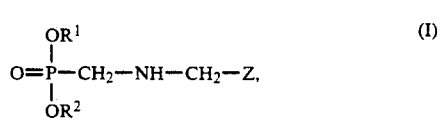

(I)

wherein:

Z is a cyano group or COOR;

R is a hydrogen atom; lower alkyl; lower alkenyl; lower alkoxyalkyl; aryl having 6 to 10 carbon atoms, wherein the aryl is unsubstituted or substituted by 1 to 3 substituents chosen independently from among lower alkyl, lower alkoxy, halogen, trifluoromethyl, nitro and cyano; or a compatible cation capable of forming a salt; and $R^1$ and $R^2$, which may be identical or different, are a hydrogen atom; lower alkyl; aryl having 6 to 10 carbon atoms, wherein the aryl is unsubstituted or substituted by 1 to 3 substituents chosen independently from lower alkyl, lower alkoxy, halogen, trifluoromethyl, nitro and cyano; biphenyl; or an herbicidally-acceptable cation capable of forming a salt;

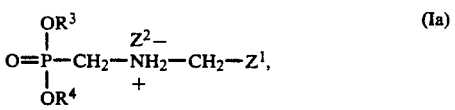

(Ia)

wherein:

$Z^2$ is a herbicidally acceptable anion capable of forming a salt;

$R^3$ and $R^4$, which may be identical or different, are a hydrogen atom; lower alkyl; aryl having 6 to 10 carbon atoms, wherein the aryl is unsubstituted or substituted by 1 to 3 substituents chosen independently from lower alkyl, lower alkoxy, halogen, trifluoromethyl, nitro and cyano; or biphenyl;

$Z^1$ is cyano or $COOR^5$; and

R[5] is a hydrogen atom; lower alkyl; lower alkenyl; lower alkoxyalkyl; or aryl having 6 to 10 carbon atoms, wherein the aryl is unsubstituted or substituted by 1 to 3 substituents chosen independently from among lower alkyl, lower alkoxy, halogen, trifluoromethyl, nitro and cyano; and (b) acifluorfen or salt thereof; wherein the weight ratio of acifluorfen or salt thereof to the glyphosate herbicide is between about 1:12 and about 1:80.

2. The herbicidal composition of claim 1, wherein the weight ratio is between about 1:15 and about 1:50.

3. The herbicidal composition of claim 1, wherein Z is COOR and Z[1] is COOR[5].

4. The herbicidal composition of claim 1, wherein R, R[1] and R[2], which may be identical or different, are a hydrogen atom or an herbicidally acceptable cation.

5. The herbicidal composition of claim 1, wherein the glyphosate herbicide is the isopropylamine cation of N-(phosphonomethyl) glycine.

6. The herbicidal composition according to claim 1, comprising between about 10% to about 50% by weight of the combination of the glyphosate herbicide and acifluorfen or salt thereof.

7. The herbicidal composition according to claim 6, comprising between about 15% to about 30% by weight of the combination of the glyphosate herbicide and acifluorfen or salt thereof.

8. The herbicidal composition according to claim 1, which is resistant to being washed out by rain after application.

9. A herbicidal product comprising the glyphosate herbicide of claim 1, acifluorfen or salt thereof and a surfactant of the ethylene oxide polycondensate type at a weight ratio of acifluorfen or salt thereof to the glyphosate herbicide between about 1:12 and 1:80.

10. The herbicidal product according to claim 9, which is applied to plants or weeds during the early leaf development stage following germination.

11. A method for the control of the growth of plants or weeds comprising the simultaneous, separate or sequential application thereto of the herbicidal product according to claim 9 during the early leaf development stage following germination.

12. A method for the control of the growth of weeds at a locus, comprising applying thereto, after post-emergence of the weeds, between about 0.1 and about 0.9 kg/ha of the glyphosate herbicide of claim 1 and between about 0.004 and about 0.08 kg/ha of acifluorfen or salt thereof, the weight ratio of acifluorfen or salt thereof to the glyphosate herbicide being between about 1:12 and about 1:80.

13. The method according to claim 12, comprising contacting said herbicide and acifluorfen or salt thereof on plants at the end of their growth cycle and/or on plants having a slower growth rate.

14. The method according to claim 12, comprising applying between about 0.4 and about 0.8 kg/ha of the glyphosate herbicide and between about 0.01 and about 0.05 kg/ha of acifluorfen or salt thereof, the weight ratio of acifluorfen or salt thereof to the glyphosate herbicide being between about 1:15 and about 1:50.

15. The method according to claim 12, comprising applying between about 0.5 and about 0.7 kg/ha of the glyphosate herbicide and between about 0.01 and about 0.05 kg/ha of acifluorfen or salt thereof, the weight ratio of acifluorfen or salt thereof to the glyphosate herbicide being between about 1:15 and about 1:50.

16. A method for the control of the growth of weeds at a locus, the weeds being at the end of their growth cycle and/or having growth slowed down by low temperatures and/or low humidity, comprising applying thereto, between about 0.1 and about 0.9 kg/ha of the glyphosate herbicide of claim 1 and between about 0.004 and about 0.08 kg/ha of acifluorfen or salt thereof, the weight ratio of acifluorfen or salt thereof to the glyphosate herbicide being between about 1:12 and about 1:80.

17. The method according to claim 16, comprising applying between about 0.4 and about 0.8 kg/ha of the glyphosate herbicide and between about 0.01 and about 0.05 kg/ha of acifluorfen or salt thereof, the weight ratio of acifluorfen or salt thereof to the glyphosate herbicide being between about 1:15 and about 1:50.

18. The method according to claim 16, comprising applying between about 0.5 and about 0.7 kg/ha of the glyphosate herbicide and between about 0.01 and about 0.05 kg/ha of acifluorfen or salt thereof, the weight ratio of acifluorfen or salt thereof to the glyphosate herbicide being between about 1:15 and about 1:50.

19. A method for reducing wash out by rainfall of the glyphosate herbicide of claim 1 after post-emergence of the weeds, comprising applying thereto, between about 0.1 and about 0.9 kg/ha of the glyphosate herbicide and between about 0.004 and about 0.08 kg/ha of acifluorfen or salt thereof, the weight ratio of acifluorfen or salt thereof to the glyphosate herbicide being between about 1:12 and about 1:80.

20. The method according to claim 19, comprising applying between about 0.4 and about 0.8 kg/ha of the glyphosate herbicide and between about 0.01 and about 0.05 kg/ha of acifluorfen or salt thereof, the weight ratio of acifluorfen or salt thereof to the glyphosate herbicide being between about 1:15 and about 1:50.

21. The method according to claim 19, comprising applying between about 0.5 and about 0.7 kg/ha of the glyphosate herbicide and between about 0.01 and about 0.05 kg/ha of acifluorfen or salt thereof, the weight ratio of acifluorfen or salt thereof to the glyphosate herbicide being between about 1:15 and about 1:50.

* * * * *